United States Patent [19]

Sakamoto et al.

[11] Patent Number: 5,678,560
[45] Date of Patent: Oct. 21, 1997

[54] BRAIN-WAVE ANALYSIS METHOD AND APPARATUS

[75] Inventors: George Sakamoto, c/o Gez Corporation, No. 801, 1-11-2-Hiroo, Shibuya-ku, Tokyo,; Morikuni Takigawa, 3-16-8, Murasakibaru, Kagoshima-shi, Kagoshima-ken; Hirotoki Kawasaki, 1-4-8-201, Minamiazabu, Minato-ku, Tokyo; Toshiyuki Sato, Tokyo, all of Japan

[73] Assignees: D F C Co., Ltd.; George Sakamoto, both of Tokyo; Morikuni Takigawa, Kagoshima-ken; Hirotoki Kawasaki, Tokyo, all of Japan

[21] Appl. No.: 567,671

[22] Filed: Dec. 5, 1995

Related U.S. Application Data

[63] Continuation of Ser. No. 106,902, Aug. 13, 1993, abandoned.

[51] Int. Cl.$^6$ ............................................. A61B 5/04
[52] U.S. Cl. .................... 128/731; 128/732; 364/413.05; 364/413.06
[58] Field of Search ........................ 128/731–732; 364/413.05, 413.06

[56] References Cited

U.S. PATENT DOCUMENTS

| 4,407,299 | 10/1983 | Culvor .................... 128/731 |
| 4,705,049 | 11/1987 | John ....................... 128/731 |
| 5,263,487 | 11/1993 | Sakamoto et al. ........ 128/731 |

*Primary Examiner*—Jennifer Bahr
*Assistant Examiner*—Stephen Huang
*Attorney, Agent, or Firm*—McGlew and Tuttle

[57] ABSTRACT

A brain-wave analysis method for analyzing a brain wave by extracting a power spectrum of the brain wave from detected brain-wave biological signals, detecting the presence or absence of peaks formed in the frequency band of each brain-wave rhythm in the power spectrum, and analyzing the brain wave based on the presence or absence of the peak spectrum; and brain-wave analysis apparatus for realizing the aforementioned method comprising a brain-wave extracting device for extracting a power spectrum with respect to a brain wave from detected brain-wave biological signals, and a peak detecting device for detecting the presence or absence of spectrum peaks formed in each brain-wave rhythm frequency band in the brain-wave power spectrum extracted by the brain-wave extracting device.

10 Claims, 4 Drawing Sheets

BRAIN-WAVE ANALYSIS METHOD AND APPARATUS

This is a continuation of application Ser. No. 08/106,902 filed Aug. 13, 1993 now abandoned.

ABSTRACT OF THE DISCLOSURE

A brain-wave analysis method for analyzing a brain wave by extracting a power spectrum of the brain wave from detected brain-wave biological signals, detecting the presence or absence of peaks formed in the frequency band of each brain-wave rhythm in the power spectrum, and analyzing the brain wave based on the presence or absence of the peak spectrum; and brain-wave analysis apparatus for realizing the aforementioned method comprising a brain-wave extracting means for extracting a power spectrum with respect to a brain-wave from detected. brain-wave biological signals, and a peak detecting means for detecting the presence or absence of spectrum peaks formed in each brain-wave rhythm frequency band in the brain-wave power spectrum extracted by the brain-wave extracting means.

FIELD OF THE INVENTION

This invention relates to a brain-wave analysis method and apparatus for performing brain-wave analysis based on the presence or absence of peaks formed in the frequency band of each brain-wave rhythm by extracting the power spectrum of brain wave from detected brain-wave biological signals.

BACKGROUND OF THE INVENTION

In recent years, an increasing number of attempts have been made to know the mental activities of human being by analyzing brain waves.

The previous analyses and studies revealed that there are four signals in a brain wave; $\alpha$, $\beta$, $\delta$ and $\theta$ rhythms, any one of which is generated or emphasized in accordance with the state of mind at the moment.

A frequency component of 0.5–3.5 Hz in a brain wave is called the $\delta$ rhythm, that of 3.5–7.5 Hz the $\theta$ rhythm, that of 7.5–13.5 Hz the a rhythm, and that of 13.5–30.5 Hz the $\beta$ rhythm, respectively.

The conventional method of detecting these four brain-wave rhythms has been such that each of the $\delta$-, $\theta$-, $\alpha$- and $\beta$-rhythm signal components is extracted, using an analog filter for each brain-wave rhythm, from small biological signals generated on electrodes pierced into the head of a subject, and those signal components are integrated.

By comparing the integrated values thus obtained, or the ratio of them, brain-wave analysis has been made; i.e., which of the brain-wave rhythms is generated, or which of the rhythms is predominant.

In the brain-wave analysis relying on the conventional method of detecting brain-wave rhythms, however, the power spectrum of a brain wave as shown in FIG. 1, for example, has often been obtained. The power spectrum shown in FIG. 1, in which only the spectrum of a large power as shown by $\delta_0$ in the figure actually existed within the $\delta$-rhythm frequency band, has been erroneously observed as if there were other spectra in the $\theta$-, $\alpha$- and $\beta$-rhythm frequency bands due to the insufficient resolution of the observation instrument.

Previous practices have been such that when the power spectrum as shown in FIG. 1 is obtained, the powers in the $\delta$-, $\theta$-, $\alpha$- and $\beta$-rhythm frequency bands are obtained separately by integrating the powers in each of the $\delta$-, $\theta$-, $\alpha$- and $\beta$-rhythm frequency bands. For this reason, despite the fact that only the power in the $\delta$-rhythm frequency band actually existed, the hatched $\theta$-rhythm region has also been erroneously recognized as being generated, leading to often different analysis results from the clinical observation results.

SUMMARY OF THE INVENTION

This invention is intended to solve the aforementioned drawback. It is an object of this invention to provide a brain-wave analysis method and apparatus in which brain-wave detection is performed on the basis of the presence or absence of peaks in the spectrum formed in each of the $\delta$-, $\theta$-, $\alpha$- and $\beta$-rhythm frequency bands, and brain-wave analysis is performed based on the brain-wave detection method.

DETAILED DESCRIPTION OF THE EMBODIMENTS

Figure 2:
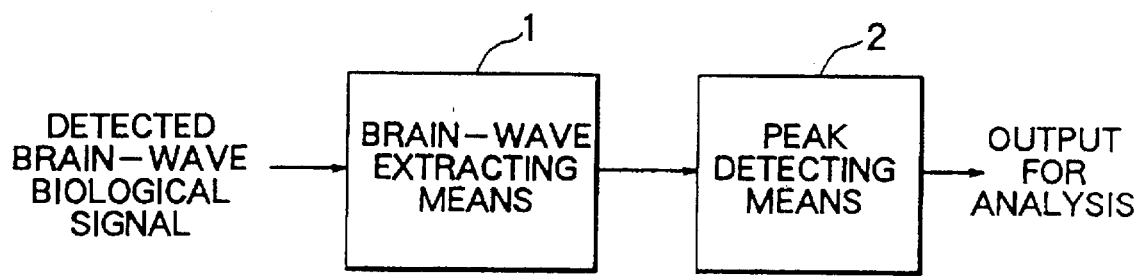
FIG. 2 is a diagram of assistance in explaining the operating principle of this invention.

FIG. 2 is a diagram of assistance in explaining the operating principle of this invention. In the figure, reference numeral 1 refers to a brain-wave extracting means; and 2 to a peak detecting means.

The brain-wave extracting means 1 receives brain-wave biological signals detected from the head of a subject, filters the biological signals with an analog or digital method, and extracts the signal components of the $\delta$, $\theta$, $\alpha$ and $\beta$ rhythms to obtain the power spectrum of the brain wave.

The peak detecting means 2 detects the presence or absence of peaks in the spectrum for each of the $\delta$-, $\theta$-, $\alpha$- and $\beta$-rhythm frequency bands in the brain-wave power spectrum obtained by the brain-wave extracting means 1. When a peak is detected, the peak detecting means 2 stores the peak value.

Figure 1:
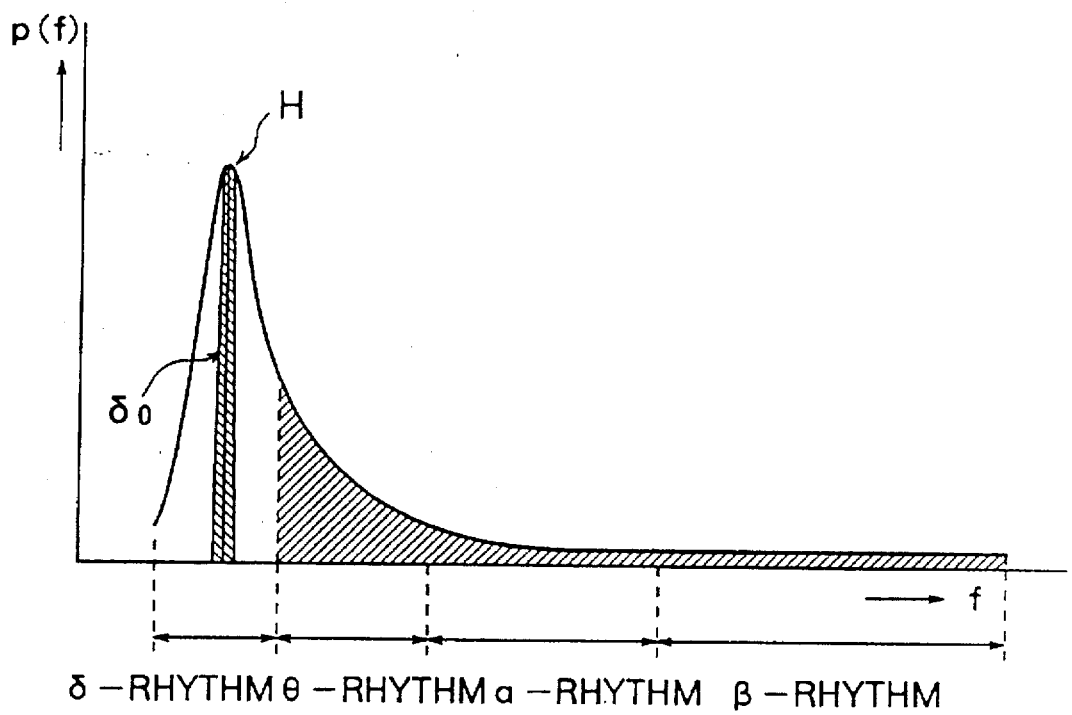
FIG. 1 is a diagram illustrating the power spectrum of a brain wave to explain the presence or absence of brain-wave rhythms.

When a peak H, for example, is detected by the peak detecting means 2 in the power spectrum shown in FIG. 1, it is concluded that the $\delta$ rhythm actually exists because the peak H is in the frequency region of the $\delta$ rhythm.

It should be noted that the peak detecting means 2 does not detect peak values, but detects the presence or absence of peak and when a peak is detected, it stops the presence of the peak and the values thereof.

Consequently, in the power spectrum shown in FIG. 1, it is judged that the $\theta$ rhythm does not exist because no peaks are found in the $\theta$-rhythm frequency band. In other words, if the resolution of the filter in the brain-wave extracting means 1 is sufficiently high, the peak H rises and falls steeply, and no peaks appear in other frequency regions. In practice, however, the spectrum curve shown in FIG. 1 is obtained because the resolution of the filter is not sufficient.

If the spectrum curve has any peak, the brain-wave rhythm of the frequency band where the peak exists is recognized as being generated actually.

Figure 3:
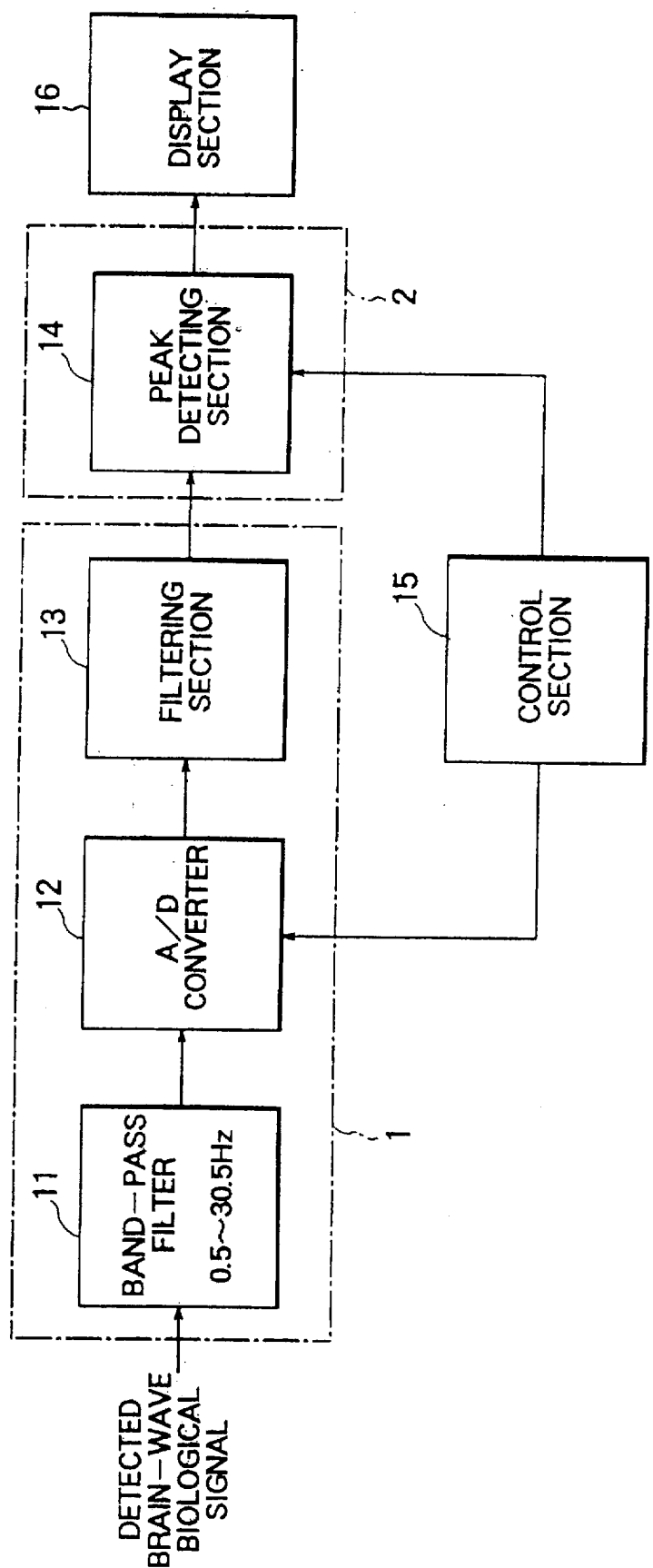
FIG. 3 is a diagram illustrating brain-wave analysis apparatus embodying this invention.

FIG. 3 is a diagram illustrating brain-wave analysis apparatus embodying this invention.

In the figure, numerals 1 and 2 correspond to the same numbers shown in FIG. 2, and 11 refers to a band-pass filter for blocking signal components other than frequencies from 0.5 Hz to 30.5 Hz; 12 to an A/D converter; 13 to a filtering section for digitally extracting a signal component of 0.5–1.5 Hz, that of 1.5–2.5 Hz, - - - that of 29.5–30.5 Hz at a resolution of 1 Hz; 14 to a peak detecting section for checking the signal components extracted by the filtering section 13 for the presence or absence of peaks in the frequency band of each brain-wave rhythm, and stores a peak value, if a peak is detected; 15 to a control section; and 16 to a display section, respectively.

The construction of the brain-wave extracting means 1 shown in FIG. 3 has been disclosed in U.S. patent application (Ser. No. 07/794,526) filed previously by the present applicant et al. In this invention, the art disclosed in the above U.S. A'pplication can be used as it is. In this Specification, therefore, the brain-wave extracting means 1 is treated as well known art, and specific description on the brain-wave extracting means 1 has been omitted.

Now, the operation of the embodiment shown in FIG. 3 will be described in the following, referring to the flow chart of an embodiment shown in FIG. 4. When the detected brain-wave biological signals processed in advance by a differential amplifier (not shown) are input to the band-pass filter 11 (Step S1), the band-pass filter 11 allows signal components in the frequency band of 0.5–30.5 Hz to pass (Step S2). The A/D converter 12 digitizes the signals fed from the band-pass filter 11 in synchronism with a timing signal from the control section 15, and transmits the digitized signals to the filtering section 13 (Step S3).

In the filtering section 13, 1-Hz wide segments of the signal components from 0.5 Hz to 30.5 Hz are extracted as described above (Step S4). The peak detecting section 14 checks the frequency component values within the δ-rhythm frequency band ranging from 0.5 Hz through 3.5 Hz for the presence or absence of peaks, based on the 1-Hz wide signal components extracted in the filtering section 13 (Step S5). When a peak is detected, the value of the peak is held as the peak δ-rhythm value (Step S6). When no peaks are detected in the δ-rhythm frequency band (Step S5), Step S7 is performed, as will be described later.

The peak detecting section 14 then checks the signal components within the θ-rhythm frequency band from 3.5 Hz through 7.5 Hz for the presence or absence of peaks (Step S7). When a peak is detected, the value of the peak is held as the peak θ-rhythm value (Step S8), and when no peaks are detected (Step 7), Step S9 is performed.

Similarly, the peak detecting section 14 checks the signal components within the α-rhythm frequency band from 7.5 Hz through 13.5 Hz (Step S9). When a peak is detected, the value of the peak is held as the peak α-rhythm value (Step S10). When no peaks are detected (Step 9), Step S11 is performed.

Next, the peak detecting section 14 checks the signal components within the β-rhythm frequency band from 13.5 Hz through 30.5 Hz (Step S11). When a peak is detected, the value of the peak is held as the peak β-rhythm value (Step S12). When no peaks are detected (Step 11), peak detecting processing is completed.

Upon completion of peak detecting processing in the peak detecting section 14, the peak detecting section 14 transmits the held peak δ-rhythm through β-rhythm values to the display section 16 for display on the display section 16, based on an instruction given by the control section 15 (Step S13).

Upon completion of this one cycle, the control section 15 transmits the digitized signal data from the A/D converter 12 to the filtering section 13 (Step S14). With this, Steps S3 through S14 will be repeated.

In order to examine the presence or absence of peaks in each of Steps S5, S7, S9 and S11, the following processing will suffice.

That is, the α rhythm, for example, corresponds to the frequency components ranging from 7.5 Hz to 13.5 Hz, and 8-Hz, 9-Hz, 10-Hz, 11-Hz, 12-Hz, and 13-Hz powers are extracted from the filtering section 13 shown in FIG. 3 as those corresponding to the α rhythm.

Needless to said, a 7-Hz power as the adjacent θ-rhythm frequency component, and a 14-Hz power as the adjacent β-rhythm frequency component are also extracted.

(Processing 1) The 7-Hz power and the 8-Hz power are compared.

(Processing 2) When the 7-Hz power is larger than the 8-Hz power, it is indicated that the power-spectrum curve has an inclination going down to the right side on the boundary between the θ-rhythm frequency component and the α-rhythm frequency component. In this case, the prerequisite for a peak to exist in the α-rhythm frequency band is that the power-spectrum curve should temporarily have the minimum value and then the maximum value in the α-rhythm frequency band, and that when comparing the maximum-value power with the 14-Hz power, which is an adjacent β-rhythm frequency component, the maximum-value power should be larger.

(Processing 3) If the 8-Hz power is lager when comparing the 7-Hz power with the 8-Hz power, the power-spectrum curve has an inclination going up to the right side on the boundary between the θ-rhythm frequency component and the α-rhythm frequency component. In this case, the prerequisite for a peak to exist in the α-rhythm frequency band is that the power-spectrum curve should have the maximum value in the α-rhythm frequency band, and that when comparing the maximum-value power with the 14-Hz power, which is a β-rhythm frequency component, the maximum-value power should be larger.

The minimum value can be examined in the following manner; i.e., if the 8-Hz power is larger as a result of comparison of the 8-Hz power and the 9-Hz power, for example, the 8-Hz power is held, and it is then compared with the next 10-Hz power, - - - . The maximum value can also be examined in the following manner; if the 9-Hz power is larger as a result of comparison of the 8-Hz power and the 9-Hz power, for example, the 9-Hz power is held, and it is then compared with the next 10-Hz power, - - - .

Figure 5:
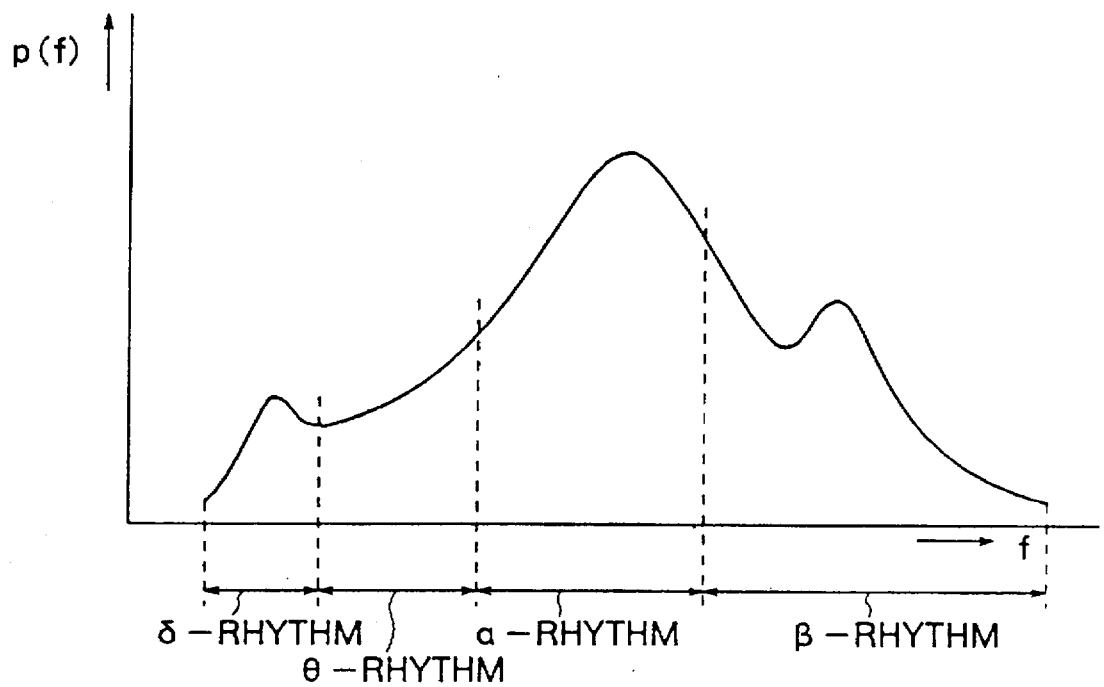
FIG. 5 a diagram illustrating an example of the power spectrum of a filtered brain wave.
Figure 6:
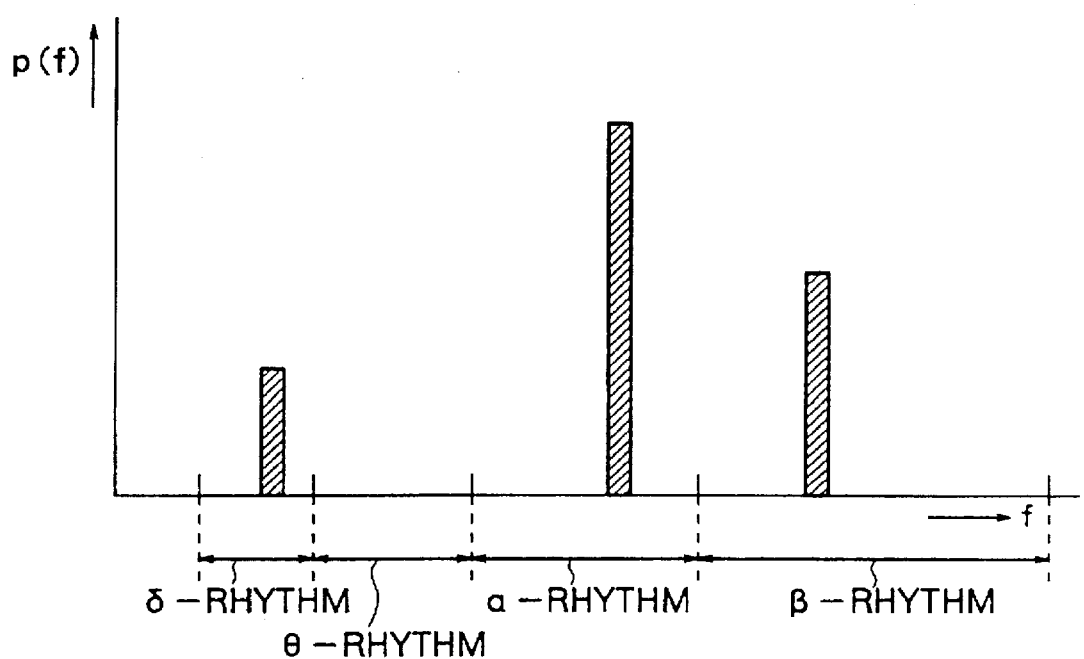
FIG. 6 is a diagram illustrating the analysis of predominance of brain-wave rhythms corresponding to FIG. 5.

Now, assuming that the power spectrum shown in FIG. 5 is extracted from the brain-wave biological signals of a subject by the filtering section 13, the predominance of brain-wave rhythms shown in FIG. 6 is displayed on the display section 16. That is, the peak δ-rhythm value, the peak α-rhythm value and the peak β-rhythm value that have been detected and held in the peak detecting section 14 shown in FIG. 3 are displayed, as shown in FIG. 6. It is indicated from this that the predominance of brain-wave rhythms is in the order of α-, β- and δ-rhythms.

When the digitized signal data from the A/D converter 12 shown in FIG. 3 is transmitted to the filtering section 13 at intervals of 1 second, for example, the predominance of brain-wave rhythms of the subject at the current time is displayed every one second, that is, in real time, on the display section 16.

Figure 4:
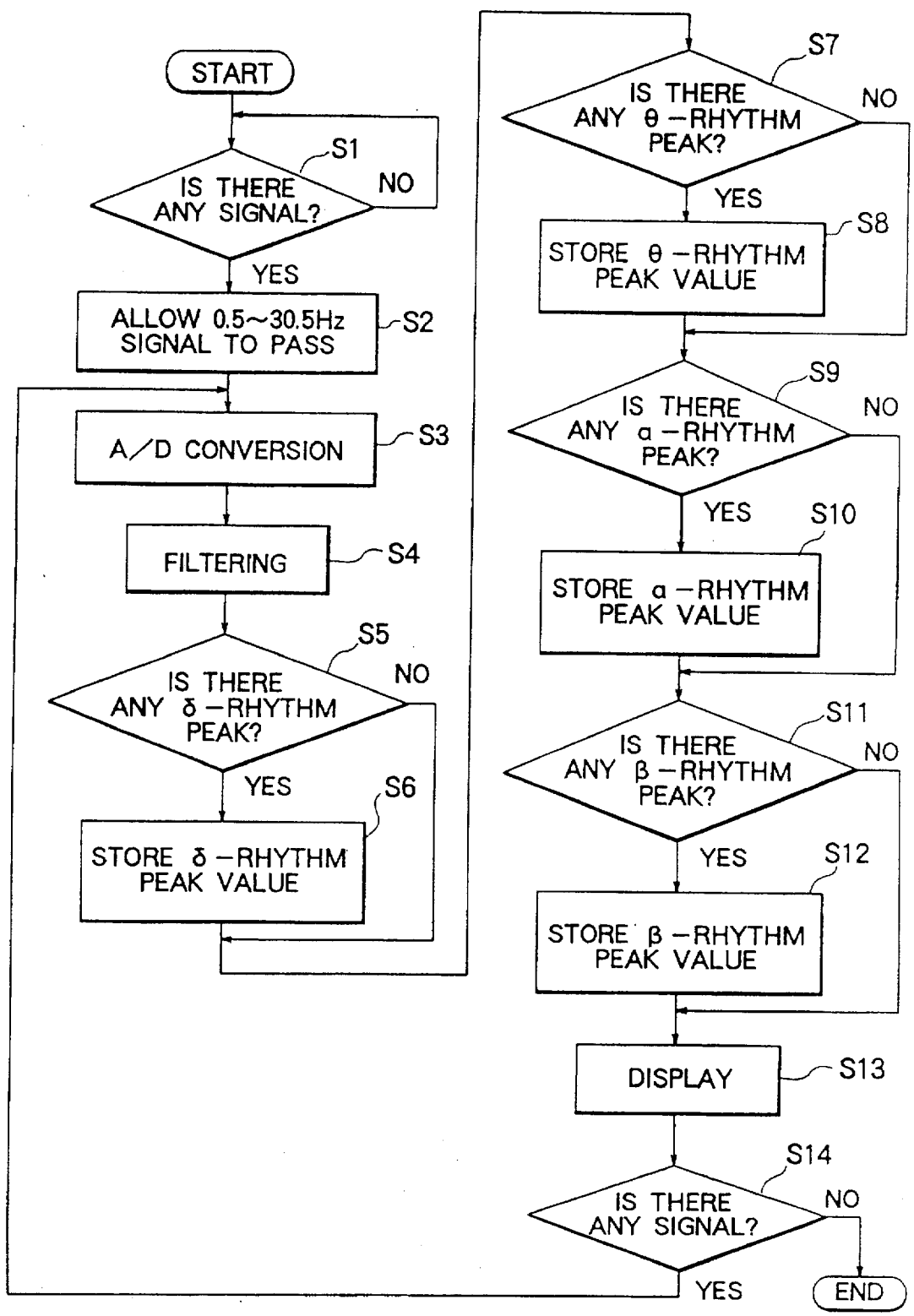
FIG. 4 is a flow chart of an embodiment of this invention.

The flow chart shown in FIG. 4 represents only an embodiment of this invention. Alternative procedures may be possible by changing the procedures from Step S5 to Step S12, that is, first checking the band 0.5-Hz to 30.5-Hz frequency band, for example, for the presence or absence of peaks, then checking a peak, if any, to see to which brain-wave frequency band it belongs, and making the display section 16 display the analysis results shown in FIG. 6.

Other analysis results can also be displayed on the display section 16 shown in FIG. 3 by adding a calculation section that relies on other analysis methods, such as ratios, weight calculation, etc., in place of the predominance of brain-wave rhythms.

Although description has been made about a signal processing method using digital filters, similar processing is possible using analog filters in place of digital filters.

As described above, this invention can analyze brain-wave rhythms basedon the presence or absence of peaks formed within the frequency band of each brain-wave rhythm, leading to good agreement between analysis results and clinical observation results.

Furthermore, this invention makes it possible to perform various analyses, other than the predominance of brain-wave rhythms by carrying out calculation in accordance with an appropriate analysis method. Thus, this invention can perform analyses with high reliability.

What is claimed is:

1. A method for analyzing brain waves, the method comprising the steps of:

detecting a brain wave signal;

filtering said brain wave signal by a plurality of band pass filters into a plurality of segments, said plurality of segments being sequential and adjacent, said plurality of segments being substantially one hertz wide and encompassing a frequency range of 0.5 Hertz to 30.5 Hertz;

grouping said plurality of segments into a plurality of bands, including a $\delta$ band containing frequencies between 0.5 Hertz to 3.5 Hertz, a $\theta$ band containing frequencies between 3.5 Hertz to 7.5 Hertz, a $\alpha$ band containing frequencies between 7.5 Hertz to 13.5 Hertz, and a $\beta$ band containing the frequencies between 13.5 Hertz to 30.5 Hertz;

determining a power spectrum for said segments as said brain wave signal passes through each of said plurality of band pass filters;

comparing magnitudes of said power spectrum from adjacent ones of said plurality of segments;

detecting a presence and absence of peak segments in said power spectrum by said comparing of magnitudes of said adjacent ones of said plurality of segments;

analyzing the brain waves by said presence and absence of peaks in said power spectrum of each of said plurality of bands, said analyzing including only indicating a brain wave presence in each of said bands if a respective said band includes a peak segment.

2. A method in accordance with claim 1, further comprising:

displaying only magnitudes of said peak segments along a frequency axis.

3. A method in accordance with claim 1, wherein:

said detecting of the brain wave signal causes a brain wave signal in one of said bands to indicate an erroneous presence of another brainwave signal in bands adjacent to said one band.

4. A method for analyzing brain waves, the method comprising the steps of:

detecting a brain wave signal;

filtering said brain wave signal into a plurality of segments, said segments being sequential and adjacent in a frequency range of 0.5 Hertz to 30.5 Hertz;

grouping said plurality of segments into a plurality of bands, including a $\delta$ band containing frequencies between 0.5 Hertz to 3.5 Hertz, a $\theta$ band containing frequencies between 3.5 Hertz to 7.5 Hertz, a $\alpha$ band containing frequencies between 7.5 Hertz to 13.5 Hertz, and a $\beta$ band containing the frequencies between 13.5 Hertz to 30.5 Hertz;

determining a power spectrum for each of said segments;

detecting a presence and location of peak segments in said power spectrum;

analyzing the brain waves by said presence of peaks in said power spectrum of said plurality of bands, said analyzing including only indicating a brain wave presence in each of said bands if a respective said band includes a peak segment.

5. A method in accordance with claim 4, further comprising:

displaying only magnitudes of said peak segments along a frequency axis.

6. A method in accordance with claim 4, wherein:

said detecting of the brain wave signal causes a brain wave signal in one of said bands to indicate an erroneous presence of another brain wave signal in bands adjacent to said one band.

7. An apparatus for analyzing brain waves, the apparatus comprising:

means for detecting a brain wave signal;

brain wave extracting means for separating said brain wave signal into a plurality of bands, including a $\delta$ band containing frequencies between 0.5 Hertz to 3.5 Hertz, a $\theta$ band containing frequencies between 3.5 Hertz to 7.5 Hertz, a $\alpha$ band contained the frequencies between 7.5 Hertz to 13.5 Hertz, and a $\beta$ band containing the frequencies between 13.5 Hertz to 30.5 Hertz each said band having a plurality of segments, said segments being sequential and adjacent in a frequency range of 0.5 Hertz to 30.5 Hertz, said brain wave extracting means also determining a power spectrum for each of said segments;

peak detection means for detecting a presence and absence of peak segments in said power spectrum by comparing individual magnitudes of said power spectrum of said segments with power spectrum magnitudes of adjacent said segments;

means for analyzing the brain waves by said presence and absence of peaks in said power spectrum of said plurality of bands, said means for analyzing including only means for indicating a brain wave presence in each of said bands if a respective said band includes a peak segment.

8. An apparatus in accordance with claim 7, further comprising:

a display means for only displaying said peak segments along a frequency axis.

9. An apparatus in accordance with claim 7, wherein:

said peak detection means displays only magnitudes of said peak segments along a frequency axis.

10. An apparatus in accordance with claim 7, wherein:

said means for detecting the brain wave signal has a resolution causing a brain wave signal in one of said bands to indicate an erroneous presence of another brain wave signal in bands adjacent to said one band.

* * * * *